United States Patent [19]
Zierdt

[11] 4,435,505
[45] Mar. 6, 1984

[54] LYSIS FILTRATION CULTURE CHAMBER

[75] Inventor: Charles H. Zierdt, Rockville, Md.

[73] Assignee: The United States of America as represented by the Department of Health and Human Services, Washington, D.C.

[21] Appl. No.: 426,141

[22] Filed: Sep. 28, 1982

Related U.S. Application Data

[63] Continuation-in-part of Ser. No. 330,020, Dec. 11, 1981, Pat. No. 4,410,630.

[51] Int. Cl.³ .............................................. C12Q 1/04
[52] U.S. Cl. .................................. 435/34; 435/287; 435/311; 436/522
[58] Field of Search ............. 435/284, 287, 296, 311, 435/34, 29, 30; 422/294–296; 436/522

[56] References Cited

U.S. PATENT DOCUMENTS 3,875,012  4/1975  Dorn et al. ................... 435/296 X
3,928,139  12/1975  Dorn ........................... 435/34
4,038,150  7/1977  Dorn et al. ................... 435/296

FOREIGN PATENT DOCUMENTS 2435524  5/1980  France ........................... 435/284

Primary Examiner—Ferris H. Lander
Attorney, Agent, or Firm—Browdy and Neimark

[57] ABSTRACT

An apparatus for blood sample treatment involves lysis, filtration and culture, the apparatus being in the form of a unitary culture chamber assembly consisting of an upper chamber for receiving a blood sample, this upper chamber receiving lysing solution squeezed from an attached bag which is subsequently detached. The upper chamber is located over and is in telescopic engagement with a lower chamber, and then vacuum is applied to the lower chamber to accomplish filtration. The lower chamber is then detached and discarded. The upper chamber is sealed and an attached bag of culture medium is squeezed to introduce the medium into the upper chamber from the bag. This second bag is detached, leaving the upper chamber as a complete blood culture system.

15 Claims, 4 Drawing Figures

LYSIS FILTRATION CULTURE CHAMBER

REFERENCE TO RELATED APPLICATION

This application is a continuation in part of copending application Ser. No. 330,020 filed Dec. 11, 1981, now U.S. Pat. No. 4,410,630, Oct. 18, 1983 the entire teaching of which is incorporated herein by reference.

FIELD OF THE INVENTION

This invention relates to apparatus for blood sample treatment, and more particularly to a unitary blood culture chamber assembly for performing a process involving the lysis, filtration and culture of a blood sample.

BACKGROUND OF THE INVENTION

In recent years an improved lysis-filtration blood culture process has been developed. A typical process of this kind is described in Zierdt et al, "Development of a Lysis-Filtration Blood Culture Technique", Journal of Clinical Microbiology, January 1977, p. 46-50, which publication is hereby included by reference.

According to the previously employed procedures, the lysis, filtration and culture are performed in separate containers as separate operations. This invites contamination, because of the many operations open to the air, pouring of the mixture from one vessel to another, and transfer of the filter membrane from the filter holder to the final culture bottle. A unitary culture chamber assembly, as described herein, would obviate almost all of this contamination risk.

SUMMARY OF THE INVENTION

In accordance with the present invention, a blood sample is subjected to (1) lysis, (2) filtration, and (3) culturing, in a unitary culture chamber assembly comprising an upper chamber for receiving the blood sample, this upper chamber receiving lysing solution squeezed from an attached flexible bag which is subsequently detached. The upper chamber has a bottom filter membrane with a bottom spout therebelow. The upper chamber is telescopically engaged with and normally located over a lower chamber. Then, vacuum is applied to the lower chamber to accomplish filtration. The lower chamber, containing the filtrate, is then slidably disengaged from the upper chamber and discarded. The bottom spout is sealingly covered by a cap, and an attached flexible bag of culture medium is squeezed to introduce the medium into the upper chamber from the bag. The second bag is detached, leaving the upper chamber as a complete blood culture system.

The above-described improved unitary system provides superior performance in that the phagocytes of the blood are killed and lysed, releasing bacteria that would otherwise be killed by phagocytic action. Other possible advantages are the removal from the blood culture of antibiotics, if present in the patient's blood. Also removed via the filtrate, which is discarded, are antibodies, complement, and opsonins. In other words, the removal is accomplished of all the anti-bacterial mechanisms of whole blood. Remaining on the filter membrane, which is then cultured, are red blood cell membranes, white blood cell membranes and nuclei, platelets, and such microorganisms which happen to be present. Although the system will trap mycoplasma and chlamydia, the bulk of microorganisms cultured are bacteria and fungi.

The present invention improves upon the invention of my co-pending patent application identified above primarily in that a needle and rubber diaphragm structure between the upper and lower chambers is eliminated. Thus elimination of parts results in a simplified apparatus with a corresponding reduction in cost of manufacture. Further, use of the device is simplified and made quicker and more fool-proof.

Accordingly, an object of the invention is to provide for improved blood sample treatment which overcomes the deficiencies and disadvantages of systems previously employed for such treatment.

A further object of the invention is to provide an improved unitary apparatus for blood sample treatment which enables the performance of blood lysis, filtration and culture in a simple and efficient manner, with minimum risk of contamination.

A still further object of the invention is to provide an improved unitary blood culture chamber assembly containing all the necessary structural elements for performing blood lysis, filtration and culture, which is relatively compact in size, which is easy to manipulate, and which enables a blood culture process to be accomplished with high efficiency and with low contamination risk.

A still further object of the invention is to provide an improved unitary blood culture chamber assembly which includes means for efficiently performing lysis of a blood sample in a main chamber, establishing communication with a vacuum filter chamber which can be subsequently removed, and for subsequently establishing the main chamber as a complete blood culture system, whereby a blood sample culture treatment can be carried out in an efficient and reliable manner.

A still further object of the invention is to provide an improved unitary apparatus for blood sample treatment which is in the form of a self-contained, easily manipulated combination of all the elements required for carrying out lysis, filtration and bacterial culture of a blood sample, and which destroys and removes phagocytes, antibodies, antibiotics, and other anti-bacterial undesired blood components, leaving red blood cell membranes, white blood cell membranes and nucleii, platelets, and such other microorganisms which happen to be present, thereby enabling efficient and reliable culture, with minimum risk of contamination of a blood sample from a patient.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
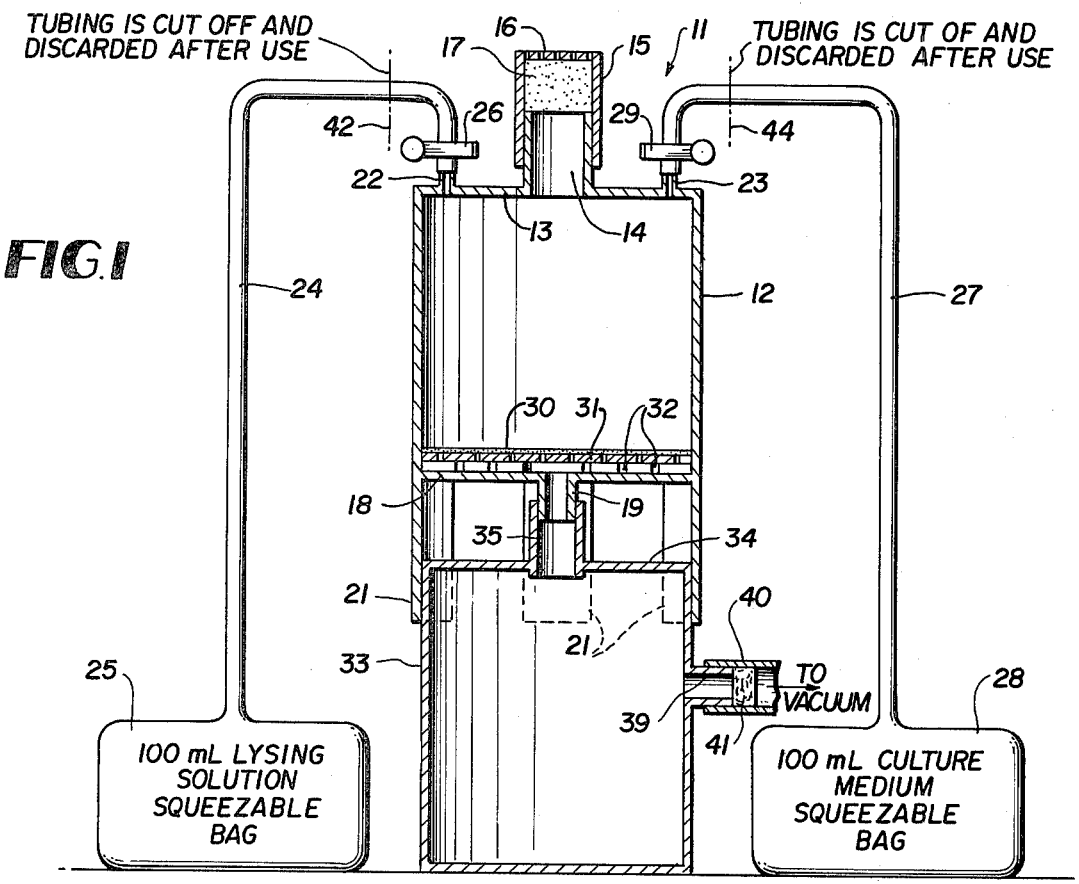
FIG. 1 is a vertical cross-sectional view taken through a typical blood sample treatment apparatus according to the present invention.

Referring to the drawings, 11 generally designates an improved blood sample treatment apparatus constructed in accordance with the present invention. The apparatus 11 comprises an upper chamber 12 which may be substantially cylindrical in shape and has a top wall 13 with an upwardly directed inlet conduit 14 normally covered by a removable cap 15 with a perforated top wall 16. The cap 15 is provided internally with a mass of porous filter material 17 which is coextensive with and located subjacent to the top wall 16, as shown in FIG. 1. Cap 15 is readily removable to allow injection of a blood sample to be processed.

Figure 2:
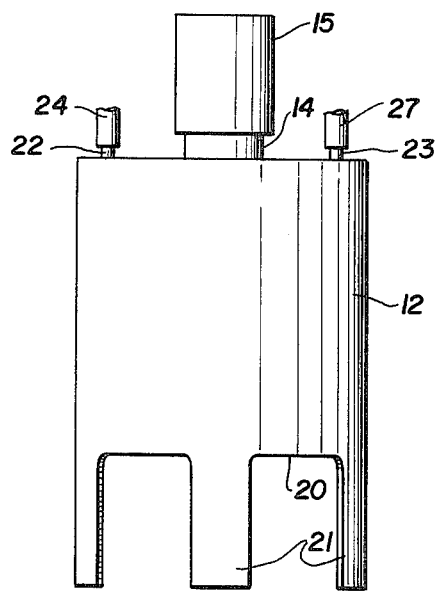
FIG. 2 is a front elevational view of the upper chamber forming part of the apparatus of FIG. 1.
Figure 3:
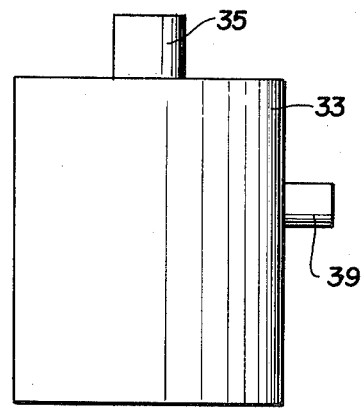
FIG. 3 is a front elevational view of the lower chamber of the apparatus of FIG. 1.

Upper chamber 12 has a bottom wall 18 formed with a central depending spout 19. The portion of the cylindrical wall of upper chamber 12 extending below the bottom wall 18 is notched out at 20 to define four evenly spaced depending supporting legs 21 of substantial length, as shown in FIGS. 1 and 2. Top wall 13 is formed with opposite upstanding inlet conduits 22 and 23. Conduit 22 is connected to a flexible plastic conduit 24 leading to a flexible bag 25 containing lysing solution, such as 0.01 M sodium phosphate buffer of pH 9.0, with 0.7% Tween 2C and Rhozyme P 11. Other known lysing solutions may be used, such as 0.1% Triton X-100 in 0.01 M $NaHCO_3$-$Na_2CO_3$ buffer, with 3% of stock Rhozyme 41 solution, as described in the above-cited Journal of Clinical Microbiology publication.

The conduit 24 is normally closed off by a conventional clamp 26 located adjacent to the chamber inlet conduit 22. The opposite conduit 23 is connected to a flexible plastic conduit 27 leading to a flexible bag 28 containing culture medium. The culture medium may be similar to that described in the above-cited Journal of Microbiology publication, or may be any other suitable culture material.

Conduit 27 is normally closed off by a conventional clamp 29 located adjacent to the chamber inlet conduit 23.

A filter membrane 30 of suitable porosity, for example, about 0.6 $\mu M$ pore membrane, is supported on a perforated disc 31 having depending short spacer pins 32 supportingly engaging bottom wall 18.

A cylindrical bottom chamber 33 is slidably and snugly received telescopically within the arcuately contoured inner surfaces of the legs 21. Chamber 33 has a top wall 34 formed with a central upwardly extending open tube portion 35 which sealingly, slidably and snugly telescopically receives the depending spout 19. The fit between the upper and lower chambers is thus maintained by the frictional engagement of legs 21 with chamber 33 and spout 19 with the inside surface of tube portion 35.

Lower chamber 33 has a side conduit 39 connected to a conduit 40 which may be at times connected to a suitable vacuum source. The connection of conduit 40 to conduit 39 includes a mass 41 of suitable filter material.

The entire apparatus 11 should be normally enclosed in a clear plastic bag, and should be suitably sterilized, such as by ethylene oxide gas, or by means of a gamma particle generator.

The following steps may be employed in the use of the lysis-filtration blood culture apparatus 11:

1. The apparatus 11 is kept on hand in the hospital ward.

2. At the time of phlebotomy, the apparatus 11 is removed from its protective container. The clamp 26 is released on the tubing 24 leading to the bag 25 of lysing solution, which is squeezed into the upper chamber 12. The clamp 26 is then reapplied to seal tube 24 and the tubing 24 is then cut off above the clamp 26, as shown at 42.

3. The top cap 15 is slipped off. From 5 to 10 ml of the patient's blood is injected into the upper chamber 12 via conduit 14. The top cap 15 is replaced, and the chamber is swirled to mix the blood and lysing solution.

4. The culture apparatus 11 (minus the bag 25) is sent to the laboratory.

5. After incubation for one hour, to permit complete blood lysis, vacuum is applied to the conduit 40, causing filtration through the filter membrane 30. Filtration only requires a few seconds.

6. The lower chamber 33 is pulled free and discarded, said lower chamber containing the filtrate resulting from the filtering and suction step. Remaining on the filter membrane 30 are red blood cell membranes, white blood cell membranes and nucleii, platelets, and microorganisms that happen to be present. The bulk of such microorganisms are bacteria and fungi.

Figure 4:
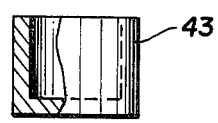
FIG. 4 is a partial cross-sectional view of the cap used to seal the upper chamber.

7. A sterile cap 43 (see FIG. 4) is slipped over the bottom spout 19 and sealingly tightened thereon. Said spout is dimensioned to make a tight frictional seal with spout 19.

8. The clamp 29 on the tubing 27 leading to the bag 28 of culture medium is released, and said bag 28 is squeezed so as to force the culture medium into the upper chamber 12. The clamp 29 is again applied and the tubing 27 is cut off upwardly adjacent to the clamp, for example, at 44 in FIG. 1.

9. The upper chamber 12, now a complete blood culture system, is placed in a 35°-37° C. incubator and observed daily for microbial growth.

While the vertically aligned chambers 12 and 33 are shown herein as being substantially cylindrical, they may take forms other than cylindrical, such as being slightly tapered, or having other than circular cross-sectional shapes.

As will be apparent by a comparison of the present disclosure with that of the parent application identified above, the primary improvement of the present invention is the elimination of the needle 37, the rubber diaphragm 38, and the bottom wall 36 of the lower chamber. In place thereof, open communication is provided between the upper and lower chambers when they are fit together as shown in FIG. 1.

Further experience with the invention forming the subject matter of both the parent and the present applications has shown that the gravity filtration that occurs during the lysis is inconsequential, and that this limited amount of gravity filtration has virtually no effect upon the lysis results nor the vacuum filtration step. Accordingly, the improvement of the present invention is this simplification of parts, corresponding reduction in cost, and simplification in use.

Referring to said prior application, step 5 in the use of that invention is essentially eliminated, the step of pressing together the upper and lower chambers to cause the needle 37 of the lower chamber to penetrate the diaphragm 38 of the upper chamber.

While a specific embodiment of an improved blood sample treatment apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. An apparatus for blood sample treatment involving lysis, filtration and culture, said apparatus comprising an upper chamber for receiving a blood sample, a first flexible bag containing lysing solution, a first flexible severable conduit connecting said first flexible bag to the upper chamber, a first removable clamp on said first flexible conduit, a second flexible bag containing culture medium, a second flexible severable conduit connecting said second flexible bag to said upper chamber, a second removable clamp on said second flexible conduit, said upper chamber having a bottom wall provided with a depending discharge spout, a filter member mounted in said upper chamber above said bottom wall, a lower chamber below said upper chamber and having a top wall provided with a tube member telescopically engaged on said discharge spout, and vacuum conduit means connected to said lower chamber.

2. The blood sample treatment apparatus of claim 1, and depending means on the upper chamber slidably and retentively engaging the outer surface of the lower chamber.

3. The blood sample treatment apparatus of claim 2, and wherein said depending means comprises a plurality of spaced leg elements depending from said upper chamber.

4. The blood sample treatment apparatus of claim 3, and wherein said lower chamber has a convexly curved outer contour and said leg elements are arcuately shaped to telescopically engage said lower chamber.

5. The blood sample treatment apparatus of claim 1, and wherein said penetrable diaphragm is sealingly secured in the bottom rim portion of said discharge spout.

6. The blood sample treatment apparatus of claim 1, and wherein said upper chamber is provided with a perforated rigid filter supporting plate-like member having depending spacer means engaging the bottom wall of the upper chamber, said filter member comprising a filter membrane supported on said perforated plate-like member.

7. The blood sample treatment apparatus of claim 6, and wherein said depending spacer means comprises a plurality of rigid pin elements depending from said plate-like member.

8. The blood sample treatment apparatus of claim 1, and wherein said discharge spout depends substantially centrally from said upper chamber bottom wall.

9. The blood sample treatment apparatus of claim 1, and wherein said upper chamber is formed with a plurality of spaced depending leg elements which are telescopically engaged with the outer surface of said lower chamber and substantially conform with the contour of said lower chamber.

10. The blood sample treatment apparatus of claim 1, and wherein said vacuum conduit means is connected to a side wall portion of said lower chamber.

11. The blood sample treatment apparatus of claim 1, and wherein said upper and lower chambers are substantially in vertical alignment.

12. The blood sample treatment apparatus of claim 11, and wherein the peripheral wall of the upper chamber is formed with a plurality of spaced downward extensions defining supporting legs, said downward extensions being slidably and snugly telescopically engaged with the lower chamber.

13. The blood sample treatment apparatus of claim 1, and a cap member for snugly sealing said tube member of said upper chamber after said uper chamber is removed from said lower chamber, whereby said upper chamber, after performance of a vacuum filtration step, can be sealed by said cap member and becomes a complete blood culture system containing the various cells and the like filtered out of said blood sample received in said upper chamber.

14. A method of treating blood samples involving lysis filtration and culture comprising the steps of providing an upper chamber for receiving a blood sample, a lower chamber for receiving vacuum pressure, selectively providing a blood sample to said upper chamber, selectively providing lysing solution to said upper chamber, providing filter means in said upper chamber at the interface between said upper chamber and said bottom chamber, providing a removable mounting of said upper chamber on said lower chamber, mixing the blood sample and the lysing solution in said upper chamber, incubating said mixture for a predetermined period of time to permit complete blood lysis, applying vacuum pressure to said lower chamber while said upper and lower chambers are sealingly fitted together to thereby cause filtration through said filter means, separating said upper and lower chambers after completion of said filtration step, sealig said upper chamber containing the portions of said blood sample not filtered through to said lower chamber on said filter member, sealing said upper chamber, providing culture medium to said upper chamber, and performing normal blood culture analysis on said sealed upper chamber.

15. The method of claim 14, wherein said lower chamber with said filtrate is discarded after said vacuum filtration step.

* * * * *